(12) United States Patent
Brant et al.

(10) Patent No.: US 6,278,975 B1
(45) Date of Patent: *Aug. 21, 2001

(54) VOICE COMMAND AND CONTROL MEDICAL CARE SYSTEM

(75) Inventors: Arthur Brant, Youngstown, OH (US); Kenneth Mandell, Sommerville, MA (US); R. Scott Rader, Baltimore, MD (US); Alexander Walsh, Hunt Valley; Eugene deJuan, Jr., Phoenix, both of MD (US); Robert Greenberg, Atlantic Beach, NY (US)

(73) Assignee: Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/377,655

(22) Filed: Aug. 19, 1999

Related U.S. Application Data (63) Continuation of application No. 08/708,015, filed on Aug. 30, 1996, now Pat. No. 5,970,457.
(60) Provisional application No. 60/006,107, filed on Oct. 25, 1995.

(51) Int. Cl.[7] .................................................... G10L 15/22
(52) U.S. Cl. ............................................................ 704/275
(58) Field of Search ................................. 704/275, 200, 704/270, 231, 271, 272, 225, 273; 381/110

(56) References Cited

U.S. PATENT DOCUMENTS

| | | | |
|---|---|---|---|
| 4,403,605 | 9/1983 | Tanikawa | 128/6 |
| 4,776,016 | 10/1988 | Hansen | 704/275 |
| 4,827,520 | 5/1989 | Zeinstra | 704/275 |
| 4,900,301 | 2/1990 | Morris et al. | 604/23 |
| 4,989,253 | 1/1991 | Liang et al. | 381/110 |
| 5,040,127 | 8/1991 | Garson | 364/513.5 |
| 5,047,009 | 9/1991 | Morris et al. | 604/23 |
| 5,181,521 | 1/1993 | Lemelson | 128/736 |
| 5,202,952 | 4/1993 | Gillick et al. | 395/2 |
| 5,245,558 | 9/1993 | Hachey | 364/708.1 |
| 5,267,323 | 11/1993 | Kimura | 704/275 |
| 5,303,148 | 4/1994 | Mattson et al. | 364/413.01 |
| 5,335,313 | 8/1994 | Douglas | 395/2.84 |
| 5,345,538 | * 9/1994 | Narayannan et al. | 704/275 |
| 5,417,210 | 5/1995 | Funda et al. | 128/653.1 |
| 5,544,654 | 8/1996 | Murphy et al. | 128/660.07 |

OTHER PUBLICATIONS

"Voice Assisted Surgery", Second International Symposium on Medical Robotics and Computer Assisted Surgery, Nov. 5–7, 1995; Baltimore, Maryland.

* cited by examiner

*Primary Examiner*—Richemond Dorvil
(74) *Attorney, Agent, or Firm*—Roylance, Abrams, Berdo & Goodman, L.L.P.

(57) ABSTRACT

A voice command and control medical care system is provided which comprises a processor having a continuous speech recognition capability. The processor is programmed to process a user's conversational speech to identify valid commands therein and to generate control signals for operating medical equipment such as surgical tools in accordance with the commands. The processor is programmed to generate audio messages reporting status information when requested, and to generate confirmation messages and await acknowledgement before executing a command. The system is configurable to interface with and control via voice activation essentially and piece of medical equipment having instruments and control switches that can be controlled via electrical or electromagnetic signals.

15 Claims, 11 Drawing Sheets

Microfiche Appendix Included
(1 Microfiche, 42 Pages)

SURGICAL INSTRUMENT STATUS

SELECTED INSTRUMENT [POSTERIOR FRAGMENTATION]

ASPIRATION LEVEL [100] mmHg  
AVERAGE POWER [0] %  
ELAPSED TIME [1:20] MIN

MAX. ASPIRATION [300] mmHg  
MAXIMUM POWER [5] %  
PULSE RATE [100] PPS

AUXILIARY INSTRUMENTS OR FUNCTIONS

BIPOLAR COAGULATION [ON]  
ILLUMINATION [0] %  
ASPIRATION PRIME [OFF]

BIPOLAR POWER [60] %  
IOP [20] mmHg

—86  
—88

VOICE RECOGNITION MODULE

USER [J. SMITH ▷]

FRAGMENTATION COMMANDS
PREMIERE SET POWER HIGH
PREMIERE SET POWER LOW
PREMIERE PULSE ON
PREMIERE PULSE OFF
PREMIERE SET ASPIRATION HIGH
PREMIERE SET ASPIRATION LOW
QUERY COMMANDS
PREMIERE REPORT POWER
PREMIERE REPORT PULSE RATE
PREMIERE REPORT ASPIRATION
PREMIERE REPORT BIPOLAR
PREMIERE REPORT IOP
MODE COMMANDS
PREMIERE GOTO SCISSORS
PREMIERE GOTO VITRECTOMY
PREMIERE END FRAGMENTATION
AUXILIARY COMMANDS
PREMIERE SET BIPOLAR HIGH  PREMIERE SET ILLUM. HIGH
PREMIERE SET BIPOLAR LOW   PREMIERE SET ILLUM. LOW
MAIN COMMANDS
STOP LISTENING

RECOGNIZED COMMAND
[PREMIERE SET POWER HIGH]

SURGICAL INSTRUMENT STATUS

SELECTED INSTRUMENT [POSTERIOR FRAGMENTATION]

| | | ELAPSED TIME [1:20] MIN |
|---|---|---|
| ASPIRATION LEVEL [100] mmHg | AVERAGE POWER [0] % | |
| MAX. ASPIRATION [300] mmHg | MAXIMUM POWER [5] % | PULSE RATE [100] PPS |

AUXILIARY INSTRUMENTS OR FUNCTIONS

| BIPOLAR COAGULATION [ON] | ILLUMINATION [0] % | ASPIRATION PRIME [OFF] |
|---|---|---|
| BIPOLAR POWER [60] % | IOP [20] mmHg | |

VOICE RECOGNITION MODULE

USER [J. SMITH] ▷

FRAGMENTATION COMMANDS
PREMIERE SET POWER HIGH
PREMIERE SET POWER LOW
PREMIERE PULSE ON
PREMIERE PULSE OFF
PREMIERE SET ASPIRATION HIGH
PREMIERE SET ASPIRATION LOW

QUERY COMMANDS
PREMIERE REPORT POWER
PREMIERE REPORT PULSE RATE
PREMIERE REPORT ASPIRATION
PREMIERE REPORT BIPOLAR
PREMIERE REPORT IOP

MODE COMMANDS
PREMIERE GOTO SCISSORS
PREMIERE GOTO VITRECTOMY
PREMIERE END FRAGMENTATION

AUXILIARY COMMANDS
PREMIERE SET BIPOLAR HIGH   PREMIERE SET ILLUM. HIGH
PREMIERE SET BIPOLAR LOW    PREMIERE SET ILLUM. LOW

MAIN COMMANDS
STOP LISTENING

RECOGNIZED COMMAND [            ]

VOICE COMMAND AND CONTROL MEDICAL CARE SYSTEM

This application is a continuation of U.S. application Ser. No. 08/708,015, filed Aug. 30, 1996 now issued as U.S. Pat. No. 5,970,457, which claims the benefit of U.S. Provisional Application No. 60/006,107, filed Oct. 25, 1995.

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyrights whatsoever.

REFERENCE TO MICROFICHE APPENDIX

Reference is made to the microfiche appendix which contains 1 sheet representing 42 frames of speech recognition software code.

FIELD OF THE INVENTION

The invention relates to a voice command and control system for controlling medical equipment.

BACKGROUND OF THE INVENTION

A number of voice assisted machine control applications have been developed due to recent advancements in speech recognition software. Examples of these applications include input and storage of electronic patient records, assistance in clinical diagnosis, generation and manipulation of medical images, and manipulation of surgical devices such as microscopes.

Voice activated control of surgical instruments for vitreoretinal surgery, for example, appears to be a good application for voice actuation technology. Intraocular surgery frequently requires simultaneous use of elaborate and sophisticated pieces of equipment by the surgeon, and coordination and integration of such equipment in an operating room with assistants and one or more nurses. A nurse is typically required to manipulate equipment controls in response to a surgeon's commands. Delays can occur when the nurse is busy setting up or adjusting other parameters when the surgeon's command is received. Delays associated with the human interface between a surgeon and a nurse can increase complexity of the surgery, particularly when conditions inside the patient's eye change rapidly and unexpectedly.

U.S. Pat. No. 4,989,253 discloses a voice control system for moving and focusing a microscope. The system is disadvantageous, however, because it employs a discrete speech recognition algorithm. An operator must therefore give simple verbal commands, which are typically only one or two words, and speak them clearly and slowly. During procedures such as intraocular eye surgery, it is difficult to expect a surgeon to speak in the slow, halting manner required for accurate word identification using a discrete speech recognition algorithm.

U.S. Pat. No. 5,303,148 discloses a voice activated image display controller which requires each operator to speak every command in order to create a stored user-specific pronunciation list. The controller compares received digitized audio signals with the list to determine if a spoken word is a valid command. The controller is disadvantageous because it requires operators to undergo time-consuming training in order to use it.

A need exists, therefore, for a voice command and control system for medical equipment which allows a surgeon to render voice commands using natural, conversational speech and which does not require the surgeon to participate in extensive training of the speech recognition engine. Further, a need exists for a voice command and control system which allows a surgeon to effectively handle volatile and quickly changing patient conditions (e.g., intraocular pressure), and to decrease surgery time without compromising the safety of the surgical procedure.

SUMMARY OF THE INVENTION

In accordance with an aspect of the present invention, a voice command and control system is provided which can process audio signals from a microphone to identify an operator's verbal commands contained within conversational speech using speech recognition software. The commands are then converted to digital control signals which can be applied to a medical care device. The system is configured to continuously monitor the audio signals such that the operator does not have to speak in a slow, deliberate and unnatural manner.

In accordance with another aspect of the invention, the system is configured to automatically generate at request for confirmation of a command signal, and to await acknowledgement from the operator before executing the command.

In accordance with yet another aspect of the invention, the system is configured to provide audible status data relating to a parameter or function of the medical care device in response to an operator's query command.

In accordance with still yet another aspect of the invention, the system is programmed to define functions and parameters of the medical care device and corresponding commands which are valid when that function or parameter is active, and to store them in files The files facilitate the speech recognition process, as well as increase safety and efficiency with which the voice controlled medical care device is used.

In accordance with an embodiment of the present invention, a voice controlled medical care system is provided which comprises (1) a medical care device to be controlled in accordance with commands spoken by an operator, the spoken commands being selected from the group consisting of a single command word, a command phrase comprising a plurality of the command words, and a mixed phrase comprising at least one command word and at least one non-command word; (2) a microphone for transducing the spoken commands and generating corresponding audio output signals; (3) a processor comprising a first port connected to the microphone for receiving the audio output signals, the processor being programmable to substantially continuously monitor the first port for the audio output signals, to process the audio output signals to identify the command words therein, and to generate corresponding control signals for transmission to the medical care device; and (4) an interface circuit connected to the processor and the medical care device and operable to provide the control signals from the processor to the medical care device.

BRIEF DESCRIPTION OF THE DRAWINGS

These and other features and advantages of the present invention will be more readily apprehended from the following detailed description when read in connection with the appended drawings, which form a part of this original disclosure, and wherein.

DETAILED DESCRIPTION OF THE PREFERRED EMBODIMENT

Figure 1:
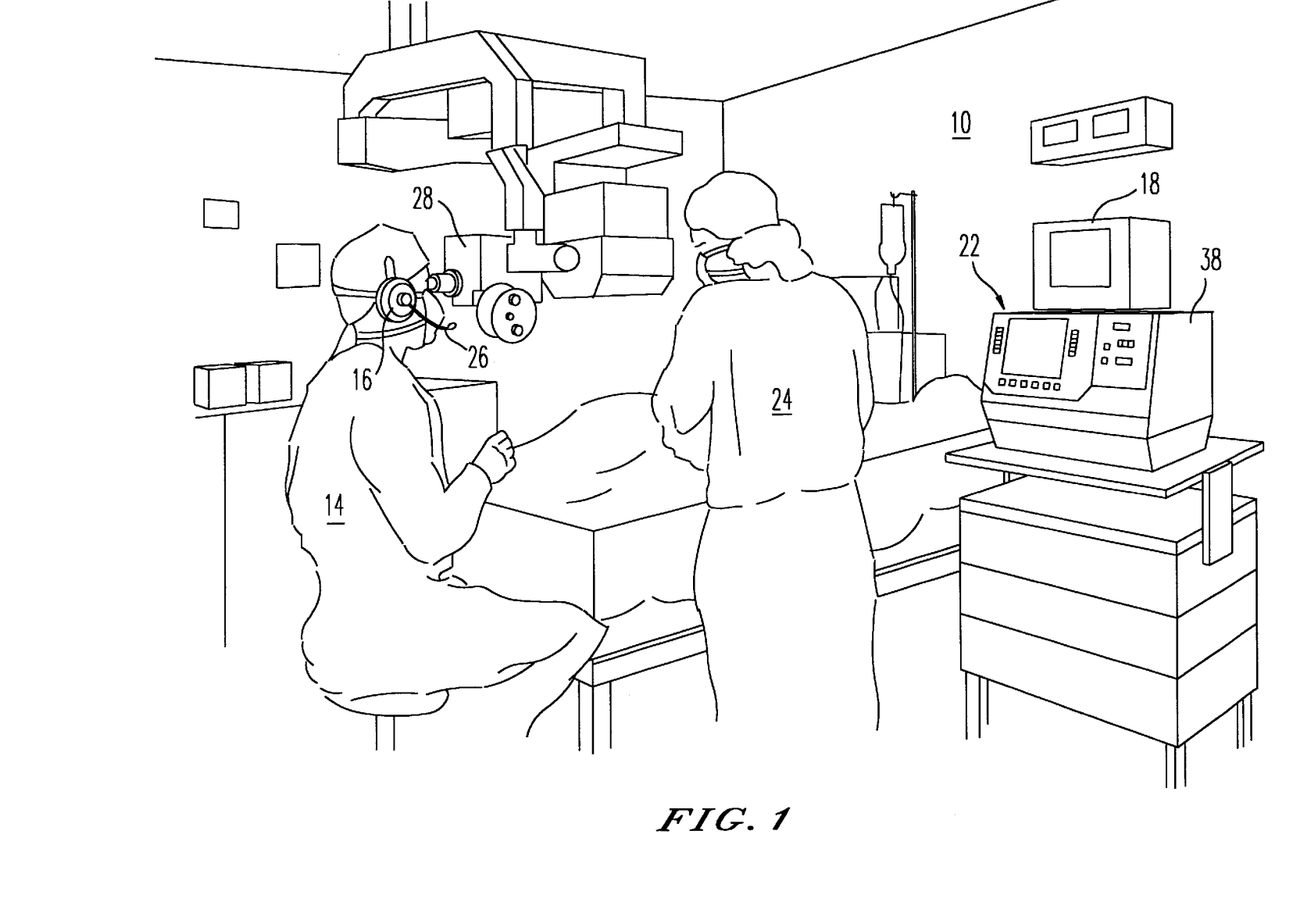
FIG. 1 depicts a voice command and control medical care system constructed in accordance with an embodiment of the present invention and in use with an intraocular microsurgical system in an operating room.

FIG. 1 depicts an operating room environment in which a voice command and control medical care system 10 is being used, in accordance with an embodiment of the present invention. The system 10 shall be described for illustrative purposes herein in connection with a Premiere® microsurgical system, which is commercially available from Storz Instrument Company, St Louis, Mo. The system 10 processes verbal commands to effect a desired change in a piece of equipment (e.g, a microsurgical system) via digital or analog circuit means. It is to be understood, however, that the system 10 can be used with other devices besides the Premiere® microsurgical system in accordance with the present invention. These other devices can include, but are not limited to, a laser, a microscope, surgical tools such as remote-controlled scissors, medical imaging devices, devices for assisting patients such as electromechanical prosthetic and mobilization tools, devices for controlling medical care environments including room lighting and air quality, patent monitoring devices such as sensors for patient vital signs, among others.

The Premiere® microsurgical system regulates speed, suction and other variables for intraocular surgical instruments which an ophthalmic surgeon holds in his or her hand during a surgical procedure. In accordance with the illustrated embodiment, a surgeon 14 or other operator of the voice command and control medical care system 10 can speak verbal commands into a headset 16 while performing surgery, as shown in FIG. 1. The system 10 comprises a computer 18, which is preferably a personal computer or a portable, laptop computer, and which is connected to the Premiere® microsurgical system 12 by an interface circuit 20 (FIG. 2) The system 10, therefore, eliminates the need to perform certain functions such as manipulating instrument panel controls (indicated generally at 22) manually, thereby allowing the surgeon 14 and any other attending medical personnel 24 freedom to manipulate devices such as handheld surgical tools and foot pedals and other operating room equipment. The system 10 can reduce burdens placed on a surgeon 14 and other medical attendants 24 during a surgical or other medical procedure, and can reduce the number of personnel required in the operating room. For example, a vitreo-retinal surgical suite is a complicated environment requiring several components of sophisticated medical equipment that are used simultaneously A nurse is typically required to manually press buttons on the Premiere® microsurgical system 12 in response to requests from the surgeon to, for example, increase the vitrectomy cut rate. In addition to the surgeon, two nurses are required throughout an operation. The system 10 is cost effective in that it can transform this environment into an operating room requiring only one nurse and the surgeon. By eliminating the human interface between the surgeon and the nurse to adjust the Premiere® microsurgical system 12, the voice command and control system 10 provides a faster and more accurate response which, in addition to the cost effectiveness of reducing personnel, optimizes surgical outcome.

Figure 2:
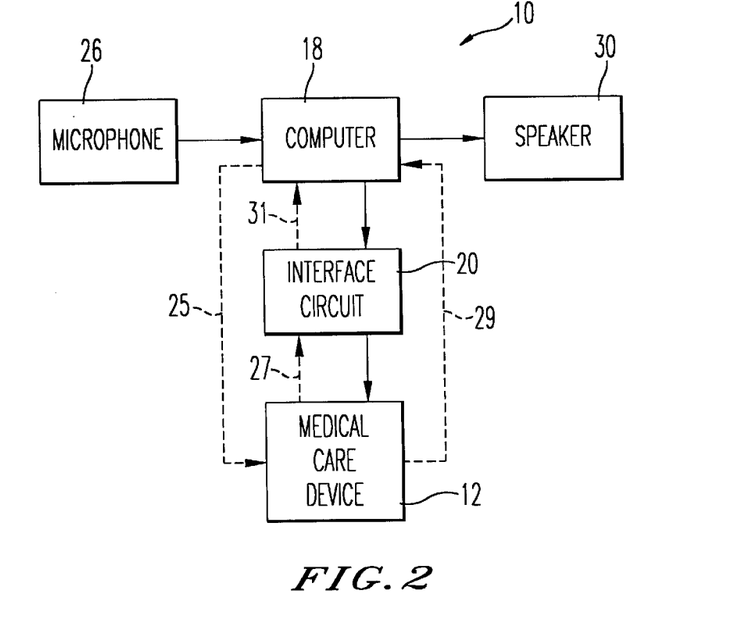
FIG. 2 is a schematic block diagram of a voice command and control medical care system in accordance with an embodiment of the invention.

FIG. 2 is a schematic block diagram of the voice command and control medical care system 10. Operator voice commands are provided to a microphone 26 which is connected to the computer 18. The transduced audio signals received from the microphone 26 are processed in accordance with speech recognition software The system 10 preferably uses Listen® for Windows® version 2.0 by Verbex Voice Systems, Inc., Edison, N.J. The Listen® for Windows® software is user-independent to accommodate many surgeons or operators, without requiring extensive voice training prior to use. The accuracy without training is approximately 80% to 90% for all users. The accuracy can be improved to approximately 100% when operators undergo training for less than one half hour to build an individual vocal profile. The refined operator specific grammar is saved in the memory of the computer or on magnetic disc or other storage device (e.g., a nonvolatile random access memory device) and can be utilized whenever that particular operator is using the system 10.

Listen® for Windows® provides a continuous versus discrete speech recognition algorithm. The software therefore allows an operator 14 to speak to the computer 18 in a natural and continuous manner, e.g., as a surgeon would normally speak to a nurse. Discrete algorithms for speech recognition are less effective than continuous speech recognition algorithms because they require users to speak more slowly and in a hesitant manner. Further, users typically speak only one or two words at a time. Surgeons may not be able to speak in the unnatural and discrete manner required for accurate recognition by discrete voice recognition algorithms during stressful situations encountered in an operation.

With continued reference to FIG. 2, the microphone 26 is preferably a unidirectional, noise canceling microphone Model PN 42446-02-00 available from CTI Audio, Inc., Conneaut, Ohio. This microphone is preferred because it can specifically amplify the operator's commands only and is designed to reduce noise. The microphone 26 can be worn as a headset microphone 16, or can be permanently mounted on an operating room microscope 28 as shown in FIG. 1. The computer 18 is preferably an IBM Think Pad laptop computer because it is portable, has multimedia capabilities allowing it to receive microphone input signals, and has an Intel 486 DX33 processor which provides for efficient execution of both speech recognition and digital conversion programs. The output from the microphone is connected to the microphone jack on the multimedia laptop computer 18.

As shown in FIG. 2, the computer 18 comprises or is connected to a speaker 30 to provide the surgeon with audible feedback and confirmation requests during the surgical procedure. The computer 18 provides control signals corresponding to an operator's verbal requests to a medical care device 12 via an interface circuit 20. In accordance with one embodiment of the present invention, the interface circuit 20 can be a hardware interface, as will be described in connection with FIG. 11. Alternatively, the computer 18 can provide control signals directly to the medical care device 12 via a serial or parallel port on the computer, as indicated by the phantom line 25. In accordance with other embodiments of the invention, the medical care device 12 can provide feedback signals to the interface circuit 20 or directly to the computer 18, as indicated by phantom lines 27 and 29, respectively, or the interface circuit can provide feedback signals to the computer 18, as indicated by phantom line 31.

Figure 3:
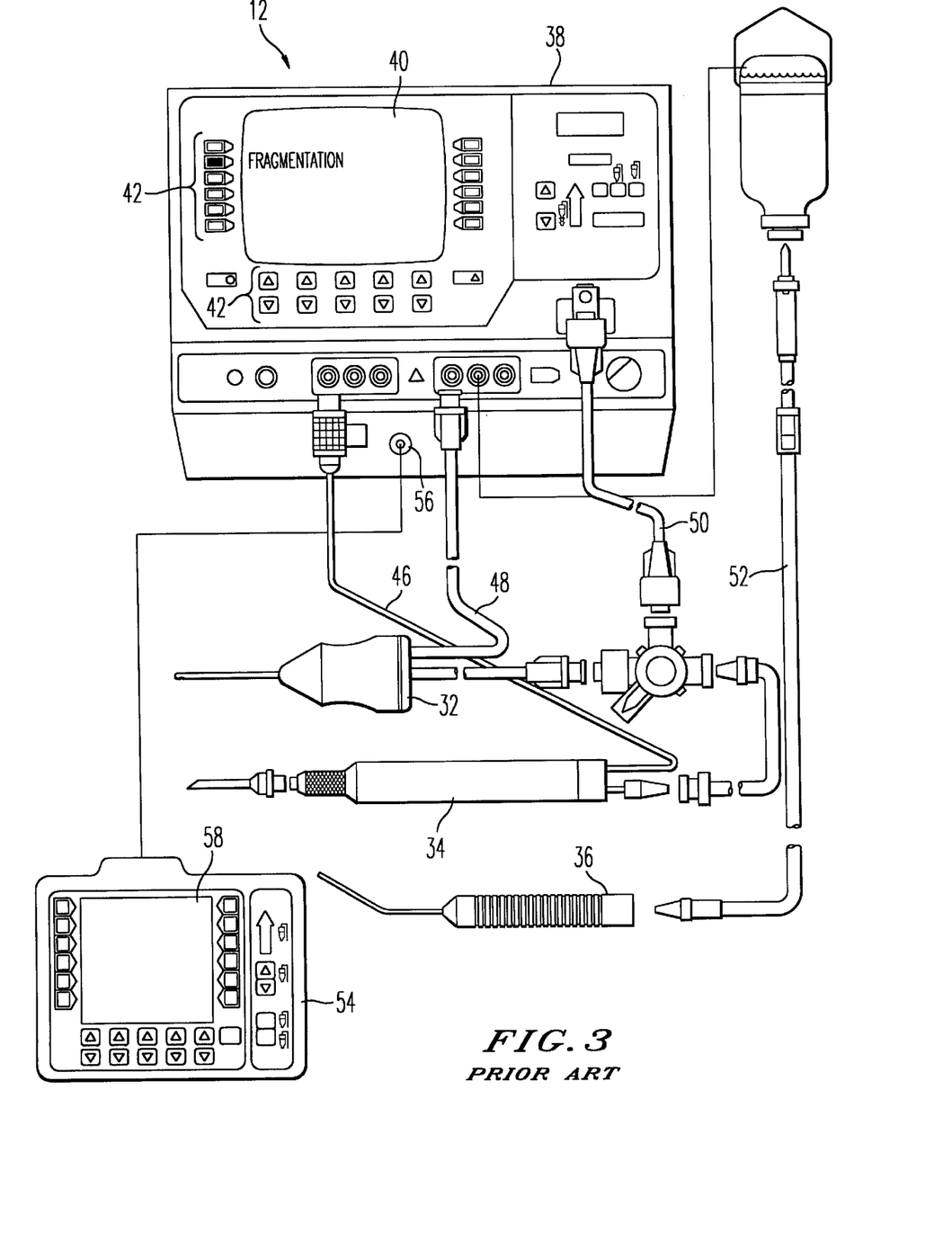
FIGS. 3 and 4 depict an exemplary and known medical care device.

With reference to FIG. 3, the Premiere® microsurgical system 12 controls a number of instruments that are placed inside the eye during vitreo-retinal surgery. These instruments can include, but are not limited to, a vitrectomy cutter 32, a fragmentation handpiece 34 and a needle 36. The microsurgical system 12 comprises a main console 38 having a display 40, a number of control buttons indicated generally at 42, and connectors for connecting an electrical line 46, an air line 48, an aspiration line 50, and an irrigation line 52, among others, to different surgical instruments. The microsurgical system 12 further comprises a remote controller 54 that can be connected to the main console 38 via a single plug connector 56. The remote controller has a display 58 that is similar to the main console display 40.

Figure 4:
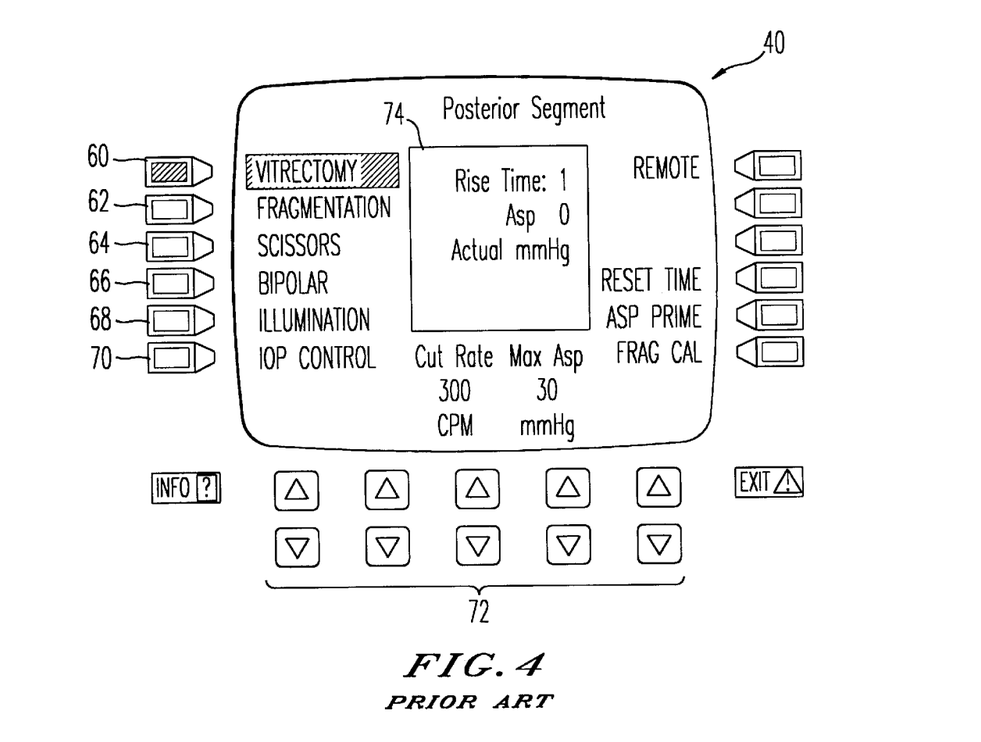

As indicated in FIG. 4, the main console display 40 comprises function select switches 60, 62, 64, 66, 68, and 70 for operating the microsurgical system 12 in a number of modes, including Vitrectomy, Fragmentation, Scissors, Bipolar, Illumination and Intraocular Pressure (IOP) Control modes, respectively. The main console also has a number of input switches (e.g., ten input switches) 72 for controlling levels of variable functions such as aspiration and cut rate. The functions of these ten switches is determined by software used to control the microsurgical system 12. The functions of the switches changes with each screen 74 presentation.

With continued reference to FIG. 3, essentially any mode or feature can be selected, or any parameter level adjusted, using either the main console 38 or the remote controller 54. When a mode (eg., Vitrectomy mode) is selected from either the console 38 or the remote controller 54, the mode is highlighted on the console screen, as indicated in FIG. 4, and flashes on the remote controller display. The operational modes of the microsurgical system 12 associated with normal posterior eye surgery will now be described for illustrative purposes. In the Vitrectomy mode, the microsurgical system 12 allows for vitreous cutting via the cutter 32 and for linear control over aspiration. In the Fragmentation mode, the microsurgical system 12 provides for phacofragmentation with linear control of aspiration for posterior segment procedures. The Scissors mode allows a surgeon to employ a pneumatically driven intraocular scissor instrument in single-cut, variable rate and proportional control modes. In single-cut control mode, scissors close rapidly when actuated and remain closed until deactivated. In variable rate control mode, scissors open and close automatically at a cyclical rate established by a cut-rate display on display 40. In proportional control mode, scissors open and close in proportion to the level of actuation (e.g., the position of a foot pedal, or length or magnitude of an actuating control signal).

As stated previously, the main console 38 comprises push buttons or switches 42 (FIG. 3) for selecting operational modes and various parameters, and for increasing or decreasing the value of parameters. The remote controller 54 can facilitate activation of these buttons 42 via the computer 18 In the past, a surgeon mentally decides on a value for each parameter such as bipolar power, cutting rate or maximum aspiration rate and conveys this selection verbally to a scrub nurse. The scrub nurse then interprets the verbal command and pushes the appropriate button on the main console 38 to select the desired parameter or to change the value of a given parameter. The surgeon does not manually make the parameter or value change because he or she does not want to direct attention away from the microscope and the operation, while holding surgical instruments inside a patient's eye. The voice command and control of the medical care system of the present invention is advantageous because it allows the surgeon to actuate appropriate buttons on the medical care device 12 without the nurse and by using only his voice, thereby reducing any delays in carrying out the verbal command as the command is interpreted and executed by a human being. This system 10 can therefore reduce personnel required in the operating room and the duration of the surgery.

The computer 18 preferably operates in a MicroSoft Windows® environment and has Listen® for Windows® software stored in its digital memory. In accordance with an embodiment of the present invention, the computer 18 is also provided with a custom executable program, which is written, for example, using Visual C++ developmental software, to process command words identified by the speech recognition software and to manipulate the medical care device 12 accordingly. The custom software code is provided in Appendices A and B. The overall operation of the system will be described with reference to the flowchart in FIG. 5.

Figure 5:
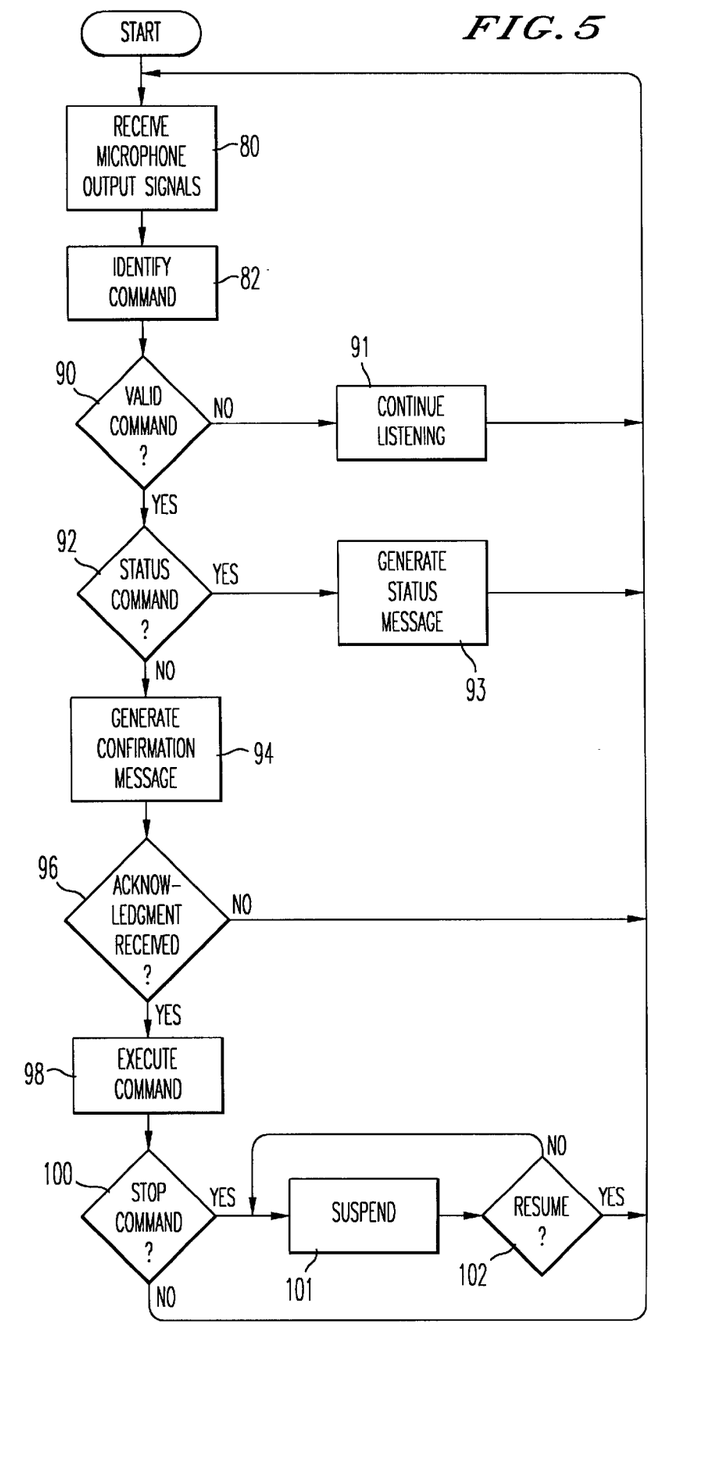
FIG. 5 is flowchart depicting the sequence of operations for processing an operator's verbal command to generate digital control signals for controlling a medical care device in accordance with an embodiment of the present invention.

As shown in FIG. 5, the computer is programmed to essentially continuously monitor its microphone input for audio output signals from the microphone 26, which transduces utterances of the operator (block 80). Because the speech recognition software has a continuous speech recognition algorithm, the verbal commands of the operator need not be as discretely or precisely stated as with a discrete speech recognition algorithm. In other words, the surgeon can intermingle actual command words with unintended words such as hesitations (e.g., "uh").

With reference to block 82 of FIG. 5; the computer analyzes the audio output signals of the microphone 26 using the speech recognition software to identify command words therein. When the voice command and control medical care system 10 is being configured for use with a particular type of medical care device 12, the functional modes of that device 12 are identified and defined, along with parameters which can or cannot be changed within those modes and restrictions, if any, on changing to different modes. Commands are subsequently defined to allow a user to initiate a particular function of the device 12, change a parameter setting or functional mode. These commands are then stored in corresponding grammar files. Appendix A contains several grammar files for using the system 10 with the Premiere® microsurgical device 12.

Figure 6:
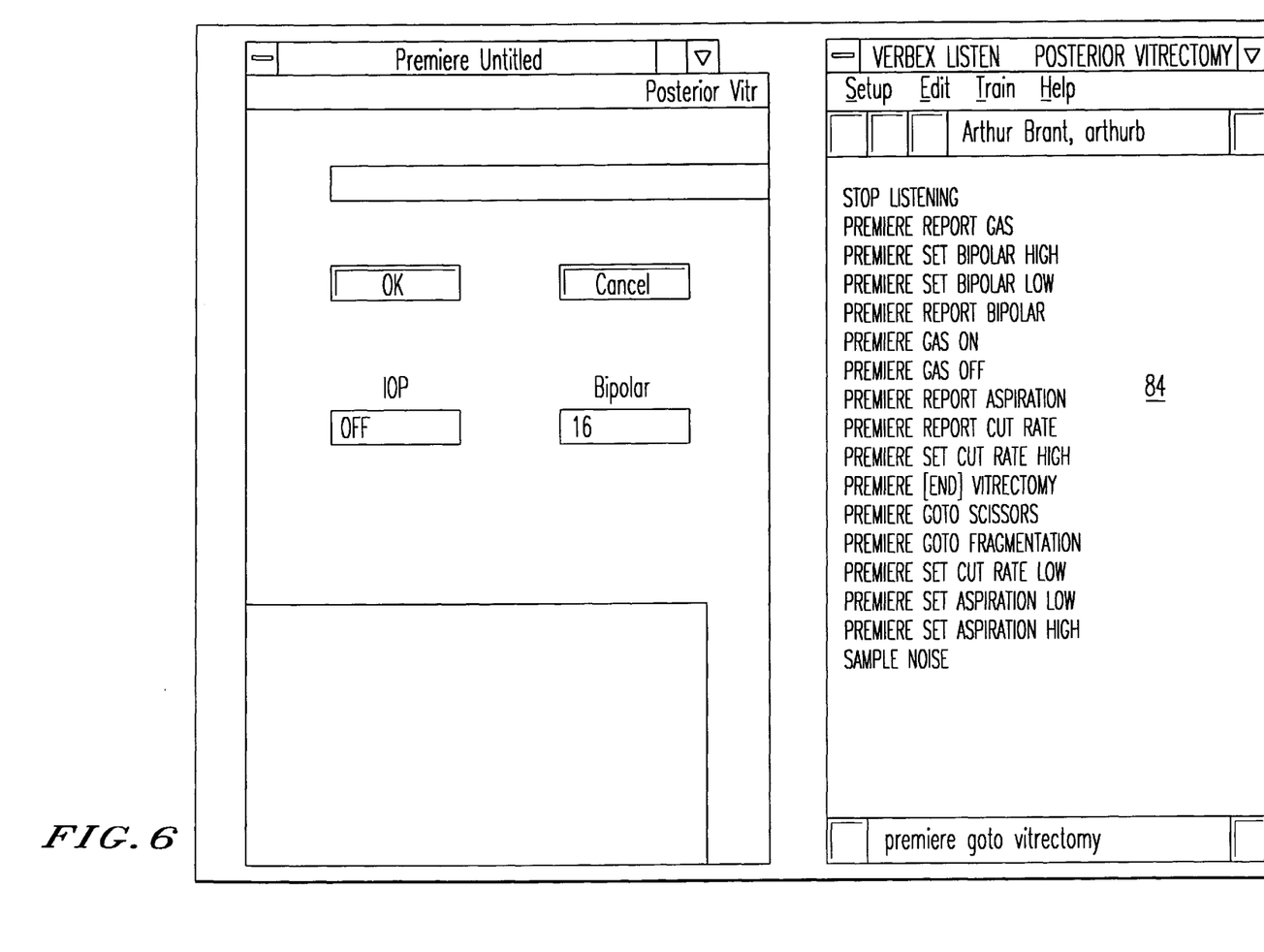
FIG. 6 depicts a computer screen generated by a voice command and control medical care system in accordance with an embodiment of the present invention.
Figure 7:
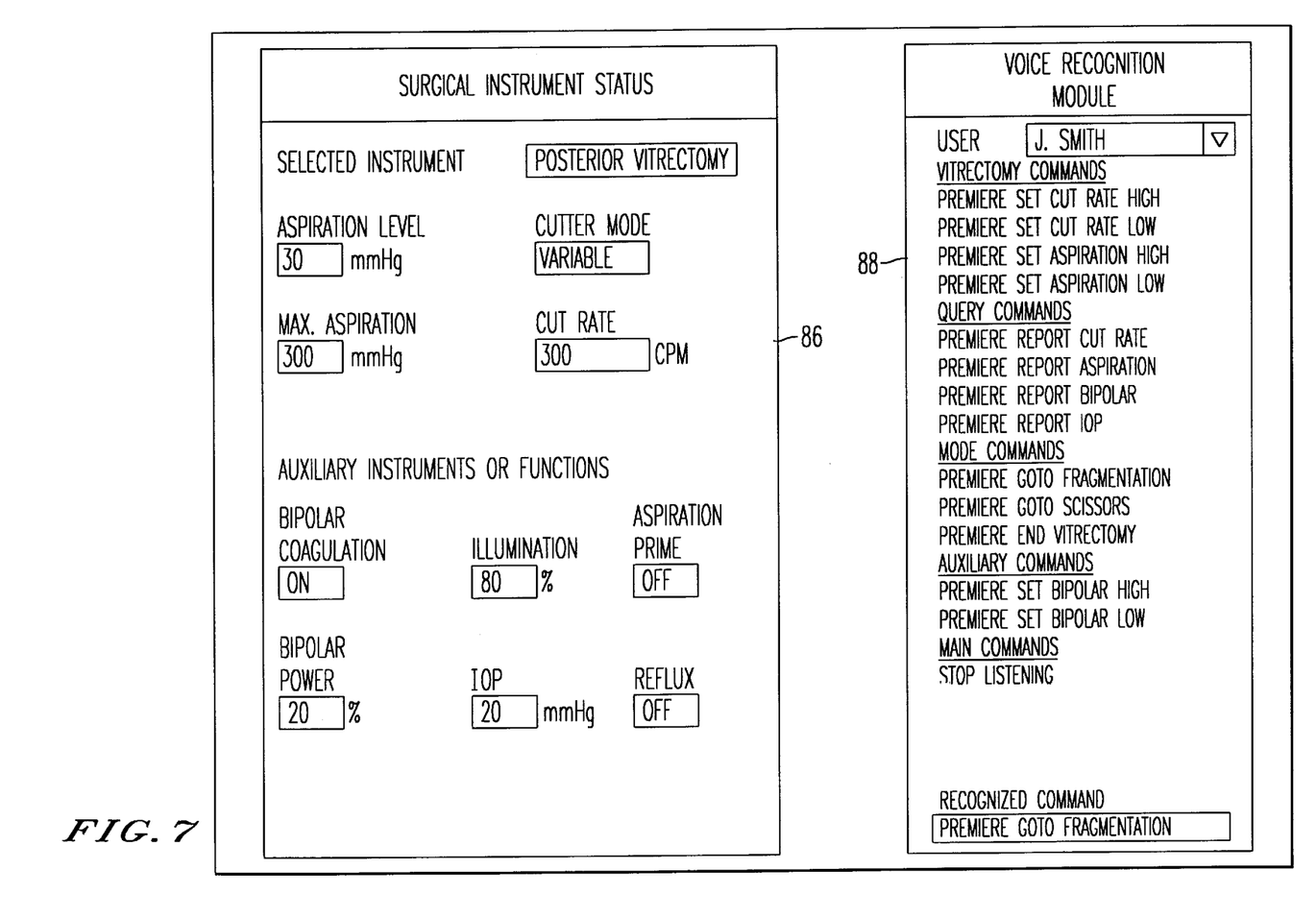
FIGS. 7, 8, 9 and 10 illustrate computer screens generated by a voice command and control system in accordance with another embodiment of the present invention.
Figure 8:
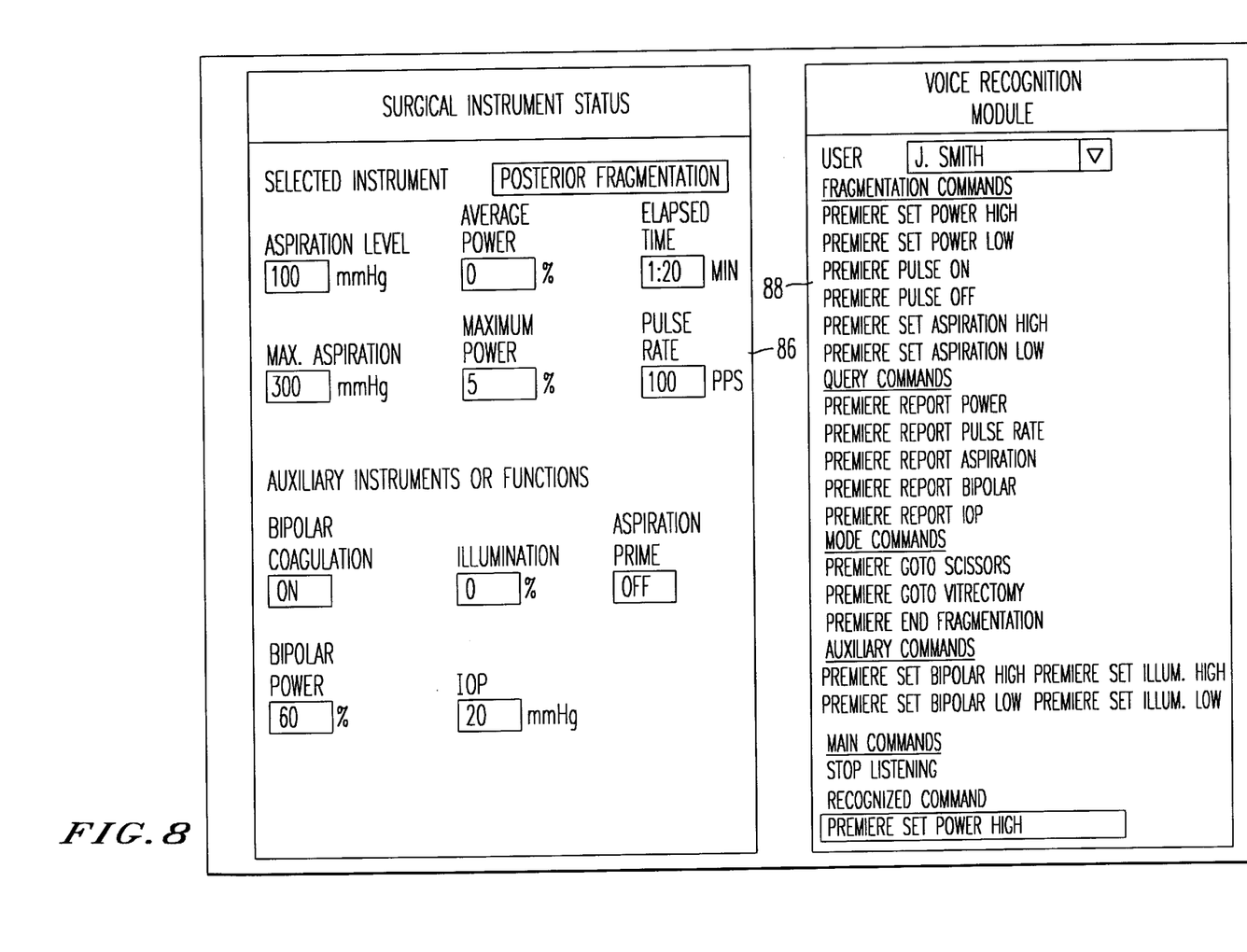

By way of example, FIG. 6 depicts a window screen on the monitor 40 of the computer 18. Against a Windows® environment background, a pop-up menu 84 is generated by the computer which lists available commands a surgeon can speak into the microphone while in the Vitrectomy mode selected and highlighted in FIG. 4. When any of these listed commands is spoken into the microphone, the computer 18 is programmed via the custom software program of the present invention to compare the audio output signal with the phrases listed in the grammar file labeled Posterior Vitrectomy Grammar in Appendix A. If the surgeon requests a change in the level of illumination (e.g., "Premiere®, set illumination high"), the computer 18 will ignore the command because it does not locate the word "illumination" in the Posterior Vitrectomy Grammar File, as indicated in blocks 90 and 91. Once a valid command is identified, the computer 18 is programmed to generate a pop-up menu corresponding to that command This is illustrated in FIGS. 7 and 8. The Premiere® microsurgical system 12 can also be used in an anterior versus posterior surgical mode to perform cataract surgery. The computer 18 is programmed to identify commands, generate screens and control medical instruments specific to the Premiere® microsurgical system when operating in the anterior surgical mode, as well as the posterior surgical mode.

FIG. 7 provides another example of a Vitrectomy mode screen. The box 86 on the left side of the screen provides status information for the selected instrument or mode (e.g., posterior vitrectomy). The computer 18 generates the status screen in accordance with data received from the medical care device 12. The computer 18 also generates the pop-up menu 88 on the right side of the screen which corresponds to the current mode or instrument function in use by the operator. The pop-up menu 88 lists commands with can be used to operate an instrument in that particular mode, to change to another mode, to request status information regarding a system function such as aspiration rate, to set a parameter level such as "Premiere® set power high" or to issue a system command such as "stop listening". If the operator gives a verbal command such as "Premiere® go to fragmentation", the computer 18 is programmed to generate the screen depicted in FIG. 8.

The status screen 86 on the left hand side of the screen in FIG. 8 gives different status information from that of FIG. 7, that is, information pertaining to posterior fragmentation. In addition, the commands for operating an instrument, setting a parameter value, inquiring about the status of certain parameters such as power, as well as auxiliary commands, change from those of the pop-up menu for the posterior vitrectomy mode in FIG. 7. For example, the parameter values for setting power or switching the pulse on or off cannot be changed when in the Vitrectomy mode. Similarly, cut rate cannot be set in the Fragmentation mode. While in the Fragmentation mode, verbal commands given by the operator are processed by the computer 18 in accordance with the speech recognition software using the grammar file for fragmentation, which is also provided in Appendix A. Thus, the speech recognition software preferably accomplishes voice controlled navigation through the various modes and parameter value changes of the medical care device 12 during a surgical procedure using a library of context-dependent command definitions stored in various grammar files.

With continued reference to the flowchart in FIG. 5, once the computer 18 identifies a valid command in an audio output signal from the microphone 26, the computer 18 is programmed to generate a confirmation message before executing the identified command, as shown in block 94, unless the command is a request for status information, as indicated in blocks 92 and 93. The confirmation messages are generated by the computer using prerecorded messages. Alternatively, synthesized speech messages can be generated by the computer 18 using appropriate software. The computer 18 is programmed to wait for acknowledgment from the operator before executing the command. Thus, the confirmation/acknowledgment feature of the system 10 increases the safety of the system, particularly in surgery, because the surgeon can cancel a verbal command, as described below.

Figure 9:
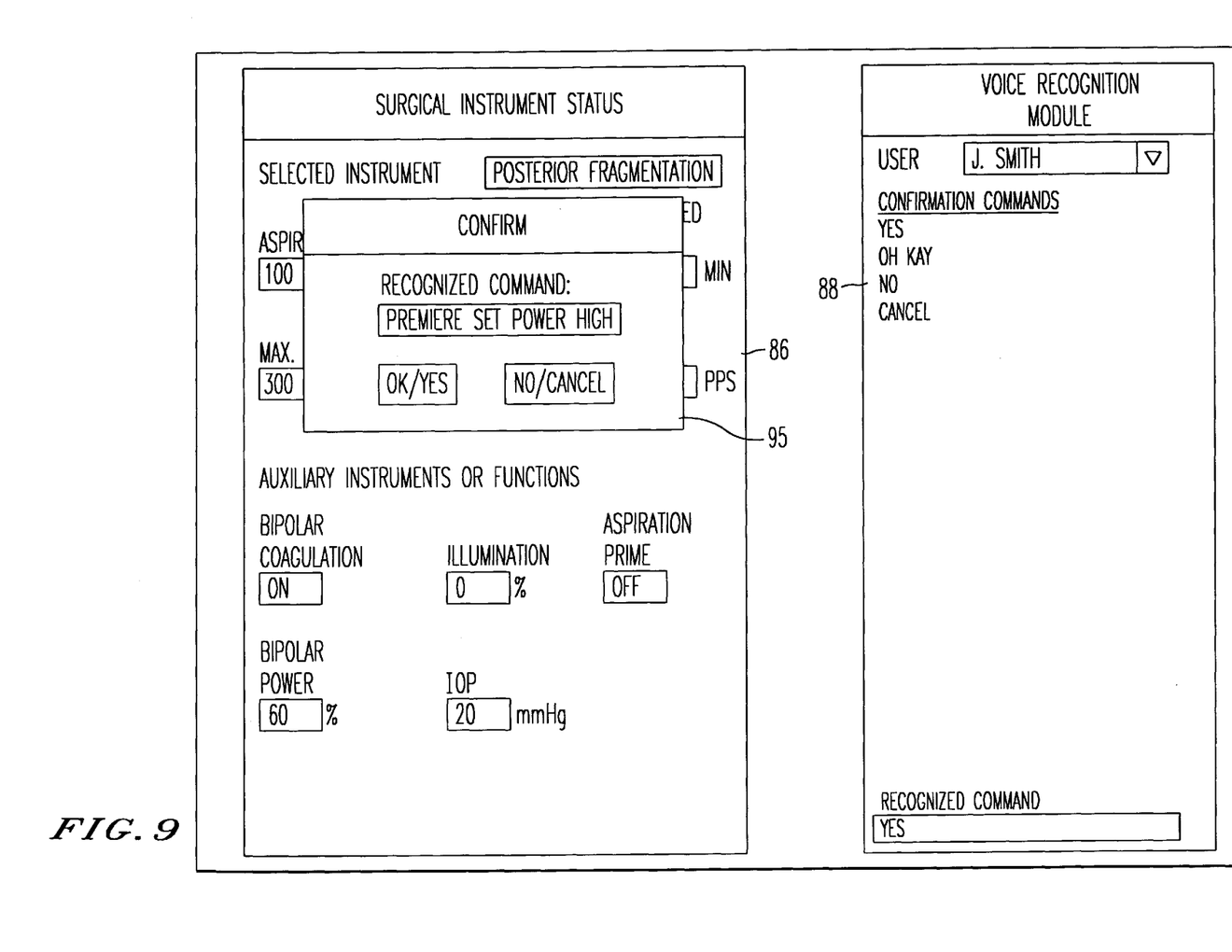
Figure 10:
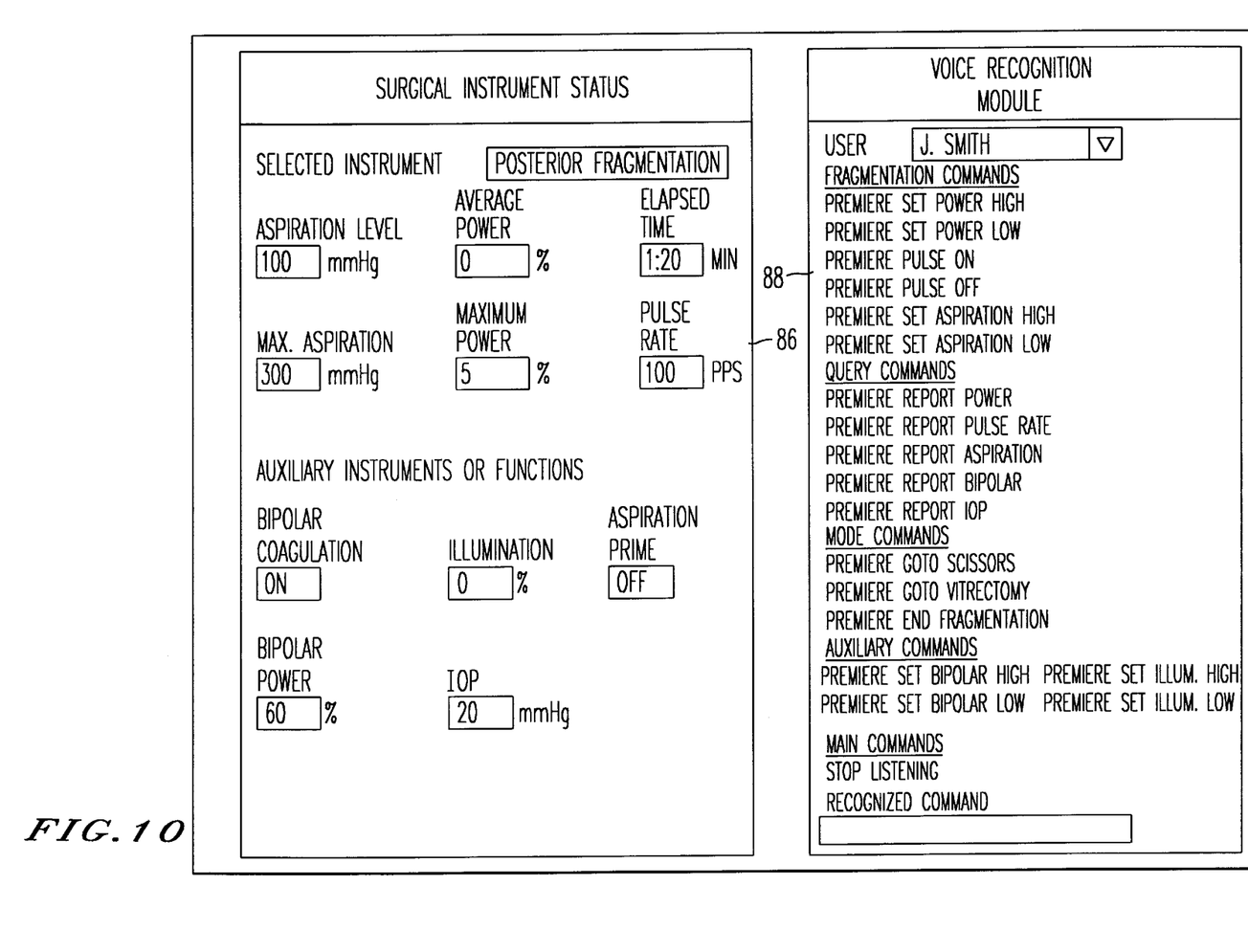

The confirmation function of the present invention is illustrated in FIG. 9. The computer 18 generates a Confirm dialogue box 95. The pop-up menu 88 on the right hand side of FIG. 9 lists valid confirmation responses or commands which can be spoken by the operator and recognized by the computer 18. If the operator responds with "yes" or "OK", the computer 18 is programmed to execute the command, as shown in blocks 96 and 98. As shown in the status screens 86 in FIGS. 8 and 10, the maximum power has been increased from 5% to 80%. The manner by which this is done will be described below in connection with FIG. 11. If the user responds with "no" or "cancel", the computer 18 is programmed to continue monitoring its microphone input for audio output signals from the microphone 26, as indicated by the negative branch of decision block 96. With reference to decision block 100, if the operator speaks the command "stop listening", the computer 18 ceases to identify commands, if any, in the surgeons conversation via speech recognition until it is commanded to resume listening, as indicated in blocks 101 and 102.

Figure 11A:
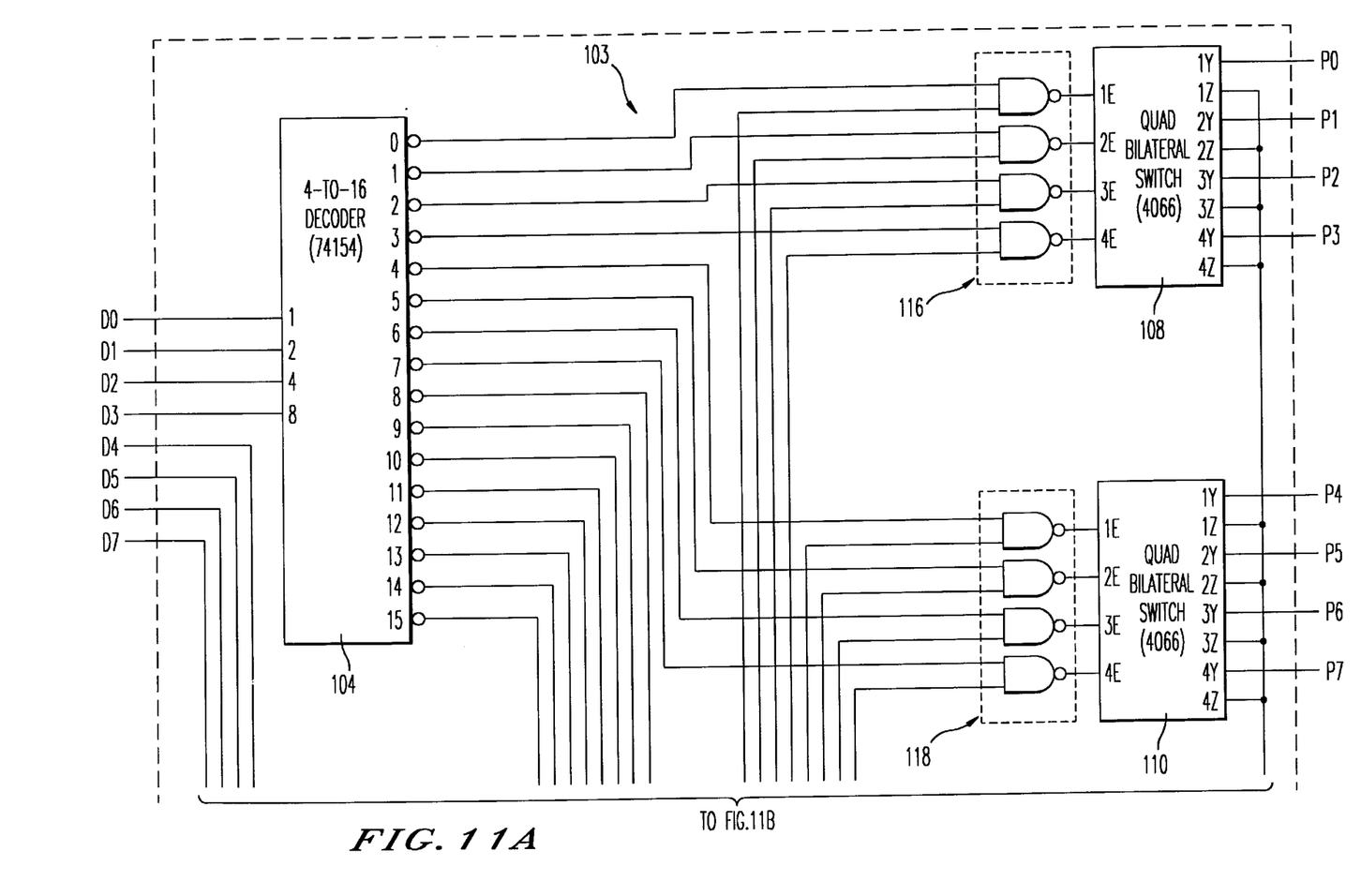
FIG. 11 is a schematic block diagram of a hardware interface for connecting a computer with a medical care device in accordance with an embodiment of the present invention.
Figure 11B:
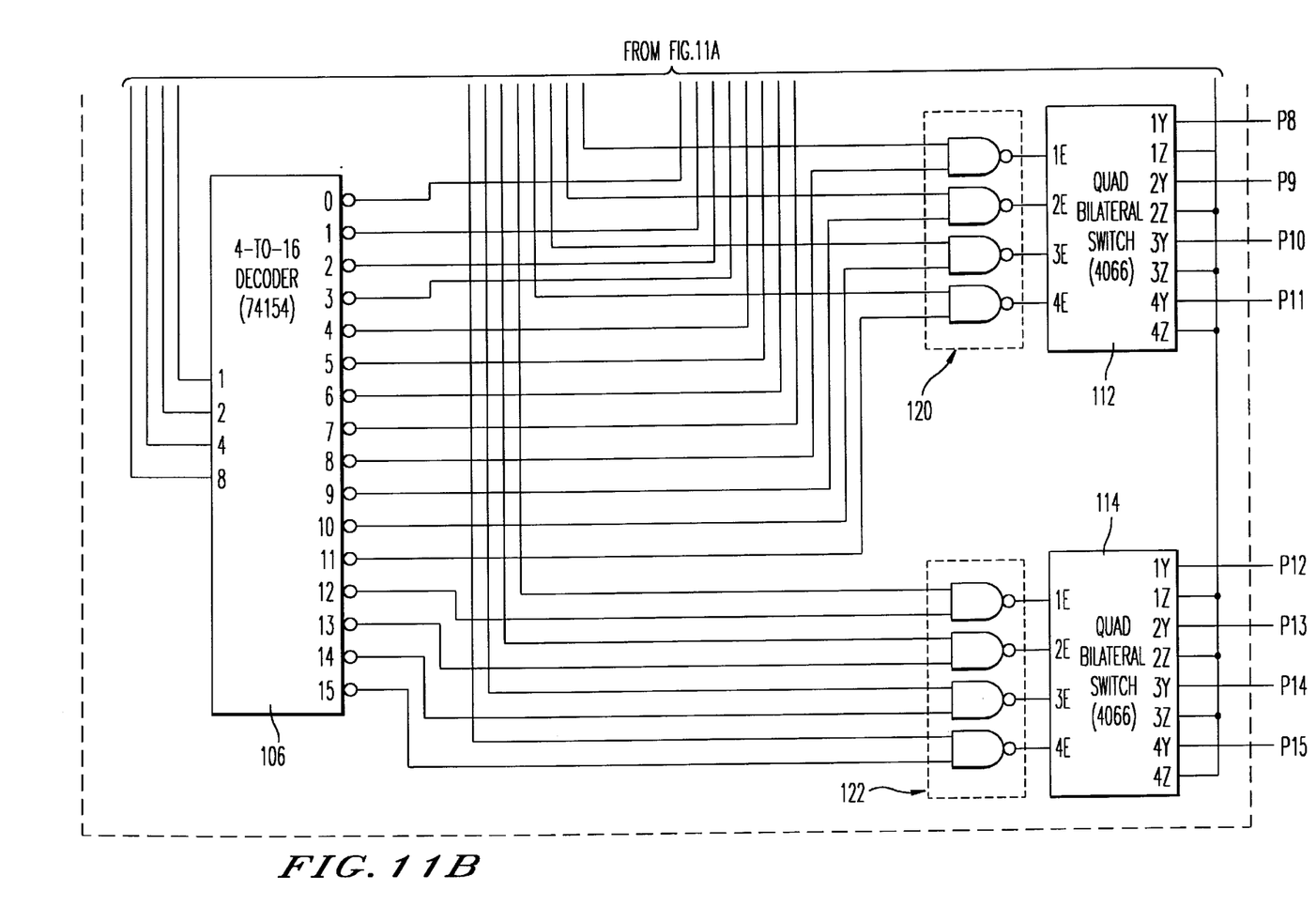

The manner in which commands are executed by computer 18 will now be described. As stated previously, when the system 10 is to be used with a particular medical care device 12, the modes of operation and possibilities for affecting changes to different parameters throughout the modes is defined (e.g., using grammar files). The method by which modes are selected and parameter values are changed within the medical care unit 12 is also analyzed. In the case of the remote controller 54 of the Premiere® microsurgical system, it was determined that pushing any of thirty buttons on the controller could be simulated electronically by shorting together various pairs of 16 wires contained within the controller 54. To enable the computer 18 to control the remote controller 54, a hardware interface 103 was designed and fabricated as shown in FIG. 11. The hardware interface 103 was placed in a black box connected to a parallel port of the computer 18 by a standard printer cable, and connected to the Premiere® remote controller 54 by a 16-pin ribbon cable. The buttons 42 on the Premiere® microsurgical system are essentially soft keys which are programmed to have multiple functions, depending on the mode in which the microsurgical system 12 is operating when a valid command is identified in the audio output signals from microphone 26. For example, one of the input switches 72 in FIG. 4 can be depressed one time in the Scissor mode to increase scissor cut rate by 30%. The same button can be depressed one time in the Phacofragmentation mode to increase ultrasound power by 1%.

Each command for a particular function is assigned a digital code which is stored in the digital memory of the computer 18. The codes can be used to affect a change to a parameter value, instrument setting or change an operational mode (e.g., selecting a different instrument).

In accordance with the illustrated embodiment of the present invention, the computer 18 is programmed to generate an 8-bit binary number corresponding to the command to be executed by the medical care device 12. The least significant bits (LSB) D0 through D3 and the most significant bits (MSB) D4 through D7 are provided to decoders 104 and 106, respectively. The decoders are connected to the inputs of four quad bi-lateral switches 108, 110, 112 and 114 via NAND gates on four quad 2-input NAND gate components 116, 118, 120 and 122, respectively. As shown in FIG. 11, each switch 108, 110, 112 and 114 has four outputs connected to the 16-pin ribbon cable and four outputs which are connected to ground.

By way of example, if a verbal command is given to set cut rate high while in the Vitrectomy mode, the computer 18 is programmed in accordance with the invention to map the command to an appropriate digital code. The code can correspond to a signal for operating one of the sixteen switches corresponding to outputs P0 through P16, for example. When activated, the switch allows an electrical signal to be applied to one of the sixteen internal wires in the controller 54 for simulating the activation of a push button on the main console 38. For example, if the button for increasing cut rate on the main console can be activated remotely by shorting together the fourth and eighth wires of the sixteen internal wires of the remote controller 54 via their corresponding switches 110 and 112, the computer 18 can output 0100B and 1000B at its parallel port. Accordingly, all of the outputs of the decoder 104 are high, except for pin number 4, which is set low. Similarly, all of the outputs of the decoder 106 are high, except for output number 8, which is set low. Each NAND gate receives a high value from the decoder outputs, except for pin numbers 4 and 8 on decoders 104 and 106, respectively The NAND gates produce a low value at the input of their corresponding switches, resulting in the switches staying open. However, switches corresponding to pins P4 and P8 of decoders 110 and 112, respectively, close since their corresponding NAND gates have one high and one low input, thus the internal wires of the controller 52 connected to pins P4 and P8 receive an electrical signal to emulate the pushing of a button on the main console 38.

It is to be understood that the number of buttons on a device 12 and the number of possible functions is arbitrary. For example, the computer 18 can be programmed to output digital signals in accordance with a matrix such that activating combinations of switches can effect different functions of the medical care device 12. In addition to providing data on a parallel port, the computer 18 can generate serial output signals which can be decoded by an interface circuit or the device 12 itself to affect desired parameter and mode changes, or other functions requested verbally by the operator. The control signals generated by the computer 18 to execute the operator's commands can be output via a parallel or serial port, can be conducted along an electrical wire or other communication link such as optical fiber. In addition, wireless communication can be used between the computer 18 and the device 12 to be controlled, such as ultrasonic signals, infrared signals, radio frequency signals or other electromagnetic signals.

The degree to which the parameters are changed can also be implemented in a number of different ways in accordance with various embodiments of the present invention. In the illustrated embodiment (FIG. 11), the closing of one of the switches corresponding to lines P0 through P15 simulates activation of a push button on the main console 38. The degree of change in the parameter variable requested by the operator is programmed and stored in the digital memory of the computer 18. Changes to parameter values are incremented such that each time a manual console button is depressed (i.e., one of the switches P0 through P15 is activated), the parameter increases or decreases from its current state by a predetermined amount. For example, if the computer 18 identifies the command "Premiere® set power high", the computer 18 is programmed to generate a control signal at the parallel port which closes appropriate switches P0 through P15 to simulate a single depression of a control button to take the medical care device 12 to the next power level, which could be an increase of 1% or 10%. Alternatively, the rate at which parameters are incremented or decremented can be done continuously, as opposed to discretely.

In addition to discrete or incremental control, the amount by which parameters can be changed can also be implemented via proportional and derivative control. For example, a parameter can increased or decreased in value in proportion to the duration of the signal being sent to the medical care device by the computer 18 or interface circuit 20. Further, feedback data can be provided to the computer 18 or other processor (e.g., a processor in the interface circuit) from the medical care device 12 for monitoring purposes. The control signal is continuously applied, or increased or decreased in magnitude, until the parameter reaches a desired threshold or another condition in the program code has been satisfied. The change in parameter value can be accomplished numerically. For example, the operator can state "Microscope, increase power thirty percent" or "Microscope, increase power three zero percent" or "three, 'oh' percent". Using the speech recognition software, the computer 18 can identify the desired level or value of a parameter from a verbal command, and then determine the amount of change required based on the current value of the parameter. The computer 18 subsequently generates and transmits one or more control signals to the medical care device 12 in order to manipulate the instrument or control button thereon and automatically jump to the desired level. Alternatively, the computer 18 can generate control signals to continuously or discretely increase or decrease the current parameter level of the instrument or control button to achieve the desired parameter level.

The interface between the computer 18 and the medical care device 12 can be implemented a number of ways such as a separate digital circuit (e.g., the circuit depicted in FIG. 11), or as components on a peripheral board inserted into a slot in a personal computer. The interface circuit can be implemented using digital or analog components or both Further, the interface between the computer 18 and the medical care device 12 can be implemented completely using software run by the computer 18. In accordance with the present invention, the system 10 can be used to interface with essentially any type of variable input or output device that can be switched or actuated by an electrical or electromagnetic signal.

As stated previously, the system 10 can be used to control a number of different devices such as medical imaging devices, surgical instruments, and environmental control equipment in operating rooms, patients' rooms and laboratories. The device to be controlled is analyzed to ascertain those functions and tools that are to be voice actuated. A vocabulary of commands is defined to control each function or tool while the tool or function is active. The tool or function-specific commands are stored in a file (e.g., a grammar file) that is accessed by the computer when processing an output signal from a microphone. The file for a particular function or tool can be defined to restrict the initiation of certain functional modes, the use of certain tools or the amount a parameter can be changed while that function or tool is active. When executing a command in a file, the computer 18 facilitates the initiation of another mode by deactivating the instrument in current use and activating relevant parameters in the new mode. The computer 18 can be programmed via the content of the files and the order with which the files and their corresponding screens (e.g., the Posterior Vitrectomy Grammar file and the active screen depicted in Fig 7) are generated to anticipate commands (i.e., to more efficiently process audio signals to identify valid commands therein), as well as to guide operator command choices, in accordance with an optimal sequence for using a medical care device 12 or performing a particular procedure such as intraocular surgery. The degree to which parameters can be changed, and the manner in which the device 12 is manipulated to affect the desired change, is defined and appropriate control signals are stored for subsequent retrieval or generation and transmission to the device 12.

The system 10 is advantageous for medical procedures such as intraocular surgery, for example, because parameters such as IOP may need to be adjusted quickly and unexpectedly during surgery. Unfortunately, the scrub nurse, who typically manipulates control buttons on medical care equipment, can be too busy setting up and adjusting other instrumentation to quickly respond to a new command, resulting in a delay in changing the parameter as needed. This can reduce the response time of the surgeon to changing conditions inside the eye and hence adversely affect the outcome of the surgery. Using the system 10 of the present invention allows changes to be made in chosen parameters directly by the surgeon, while allowing him or her to continue holding surgical instruments inside the eye. Further, the surgeon does not have to direct attention away from the patient and the microscope view to ascertain the value of a parameter. Following a query command, the computer 18 automatically generates a status report, using pre-recorded or synthesized messages and pronunciations of numerical values, which is broadcast over the speaker 30 (FIG. 2). The above-described features increase the safety of the medical procedure being performed using the voice controlled medical care system 10 of the present invention.

While certain advantageous embodiments have been chosen to illustrate the invention, it will be understood by those skilled in the art that various changes and modifications can be made herein without departing from the scope of the invention as defined in the appended claims.

What is claimed is:

1. A voice controlled medical care system comprising:
    a medical care device to be controlled in accordance with commands spoken by an operator, said spoken commands being selected from the group consisting of one of a number of different command words, a command phrase comprising a plurality of said command words, and a mixed phrase comprising at least one of said command words and at least one non-command word;
    an audio transducer for transducing said spoken commands and generating corresponding audio output information; and
    a processor comprising a first port in communication with said audio transducer for receiving said audio output information said processor being programmable to monitor said first port for said audio output information, to process said audio output information to identify said command words therein, and to generate corresponding control signals for transmission to said medical care device.

2. A voice controlled medical care system as claimed in claim 1, wherein said processor comprises at least one port selected from the group consisting of a serial port and a parallel port, and said medical care device is connected to said processor via said port to receive said control signals.

3. A voice controlled medical care system as claimed in claim 1, wherein said processor is operable to generate said control signals in a signal type selected from the group consisting of an electrical signal, an infrared signal an ultrasonic signal, a radio frequency signal, and an electromagnetic signal.

4. A voice controlled medical care system as claimed in claim 1, wherein said medical care device comprises at least one controllable device selected from the group consisting of a variable input device and a variable output device, and further comprising an interface circuit connected to said processor and said medical care device for operating said controllable device in accordance with said control signals.

5. A voice controlled medical care system as claimed in claim 4, wherein at least one of said processor and said interface circuit is operable to generate said control signals in a signal type selected from the group consisting of an electrical signal, an infrared signal an ultrasonic signal, a radio frequency signal, and an electromagnetic signal.

6. A voice controlled medical care system as claimed in claim 1, wherein said spoken commands each comprise identification of said medical care device followed by a function of said medical care device that is being requested by said operator.

7. A voice controlled medical care system as claimed in claim 1, wherein said medical care device is an active surgical instrument, said processor being programmable to generate said control signals to control said surgical instrument during a surgical procedure.

8. A voice controlled medical care system as claimed in claim 1, wherein said medical care device is selected from the group consisting of a laser, an environmental control system, a surgical tool an imaging device, a microscope, patient prosthetic device, a patient mobilization device, and a patient monitoring device.

9. An apparatus for controlling a medical care device that is controllable via commands spoken by an operator, the apparatus comprising:
    an input for receiving audio output information corresponding to said spoken commands when said spoken commands are transduced, said spoken commands comprising at least a mixed phrase having at least one of a number of different command words and at least one non-command word;
    a processing device programmable to essentially continuously monitor said input for said audio output information, to process said audio output information to identify said command words therein, and to generate corresponding control signals for transmission to said medical care device.

10. An apparatus as claimed in claim 9, wherein said processing device comprises at least one output selected from the group consisting of a serial port and a parallel port, and said medical care device is connected to said processor via said port to receive said control signals.

11. An apparatus as claimed in claim 9, wherein said processing device is operable to generate said control signals in a signal type selected from the group consisting of an electrical signal an infrared signal an ultrasonic signal, a radio frequency signal, and an electromagnetic signal.

12. An apparatus as claimed in claim 9, wherein said medical care device comprises at least one controllable device selected from the group consisting of a variable input device and a variable output device, and further comprising an interface circuit connected to said processing device and said medical care device for operating said controllable device in accordance with said control signals.

13. An apparatus as claimed in claim 12, wherein at least one of said processing device and said interface circuit is operable to generate said control signals in a signal type selected from the group consisting of an electrical signal, an infrared signal, an ultrasonic signal, a radio frequency signal, and an electromagnetic signal.

14. An apparatus as claimed in claim 9, wherein said medical care device is an active surgical instrument, said processing device being programmable to generate said control signals to control said surgical instrument during a surgical procedure.

15. An apparatus as claimed in claim 14, wherein said medical care device is selected from the group consisting of a laser, an environmental control system, a surgical tool, an imaging device, a microscope, patient prosthetic device, a patient mobilization device, and a patient monitoring device.

* * * * *